(12) United States Patent
Hart et al.

(10) Patent No.: US 7,550,200 B2
(45) Date of Patent: Jun. 23, 2009

(54) MICROENCAPSULATION OF BIOCIDES AND ANTIFOULING AGENTS

(75) Inventors: Ronald Lee Hart, Xenia, OH (US);
David Russell Virgallito, Beavercreek, OH (US); Dale Ellis Work, London, OH (US)

(73) Assignee: Microtek Laboratories, Inc., Dayton, OH (US)

( * ) Notice: Subject to any disclaimer, the term of this patent is extended or adjusted under 35 U.S.C. 154(b) by 582 days.

(21) Appl. No.: 11/226,644

(22) Filed: Sep. 14, 2005

(65) Prior Publication Data

US 2006/0063001 A1     Mar. 23, 2006

Related U.S. Application Data

(60) Provisional application No. 60/609,741, filed on Sep. 14, 2004.

(51) Int. Cl.
*B32B 27/28* (2006.01)
*A01N 25/34* (2006.01)

(52) U.S. Cl. .............. 428/402.21; 428/402.22; 428/402.2; 428/402.24; 428/402; 424/408

(58) Field of Classification Search ............ 424/408; 428/402.2, 402.21, 402.22, 402.24, 402
See application file for complete search history.

(56) References Cited

U.S. PATENT DOCUMENTS

| | | | | |
|---|---|---|---|---|
| 4,557,755 A | * | 12/1985 | Takahashi et al. | 504/359 |
| 5,225,278 A | * | 7/1993 | Kielbania et al. | 428/402.22 |
| 5,277,979 A | * | 1/1994 | Kielbania et al. | 428/402.21 |
| 6,365,066 B1 | * | 4/2002 | Podszun et al. | 252/380 |
| 6,610,282 B1 | * | 8/2003 | Ghosh | 424/78.09 |
| 7,338,928 B2 | * | 3/2008 | Lau et al. | 510/441 |
| 7,377,968 B2 | * | 5/2008 | Reybuck et al. | 106/18.33 |
| 2002/0061954 A1 | * | 5/2002 | Davis et al. | 524/474 |
| 2003/0021847 A1 | * | 1/2003 | Baxter et al. | 424/487 |
| 2004/0234603 A1 | | 11/2004 | Baum et al. | |

FOREIGN PATENT DOCUMENTS

EP     0679333     11/1995

OTHER PUBLICATIONS

Database WPI Section Ch, Week 200241 Derwent Publications Ltd., London, GB; AN 2002-377074 XP002362475 & JP 2002 053412 A (Daiwa Kagaku Kogyo KK) Feb. 19, 2002 Abstract.
Database WPI Section Ch, Week 199402 Derwent Publishing Ltd., London, GB; AN 1994-012149 XP002362476 & JP 05 320002 A (Kureha Chem Ind Co. Ltd.) Dec. 3, 1993 Abstract.
International Preliminary Report on Patenability issued regarding International Application No. PCT/US05/33109 (Oct. 9, 2007).

* cited by examiner

*Primary Examiner*—Douglas Mc Ginty
(74) *Attorney, Agent, or Firm*—Thompson Hine LLP

(57) ABSTRACT

The present invention relates to microencapsulated compositions of isothiazolone derivatives and other water insoluble biocides or antifouling agents. In particular, the present invention relates to microencapsulated 4,5 dichloro 2 n-octyl-3(2H)-isothiazolone(DCOIT), useful in marine antifouling coatings and paints.

12 Claims, No Drawings

MICROENCAPSULATION OF BIOCIDES AND ANTIFOULING AGENTS

CROSS-REFERENCE TO RELATED APPLICATIONS

This application claims the benefit of Provisional Patent Application No. 60/609,741 filed Sep. 14, 2004.

FIELD OF THE INVENTION

The present invention relates to microencapsulated compositions of isothiazolone derivatives useful as biocides or antifouling agents. In particular, the present invention relates to microencapsulated (4,5-dichloro-2-n-octyl-3(2H)-isothiazolone), and using the microcapsules in marine antifouling coatings and paints.

BACKGROUND OF THE INVENTION

The present invention relates generally to the microencapsulation of (4,5-dichloro-2-n-octyl-3(2H)-isothiazolone (DCOIT), a biocide product available from Rohm and Haas Company and analogues and derivatives thereof. Marine coating and paint manufacturers customarily add biocides to the paint to prevent or inhibit unwanted infestation of the films by microorganisms, e.g., fungi, such as molds and yeasts, and also by bacteria, algae, and cyanobacteria (so-called "soft fouling") when these paints are applied on a vessel or underwater structure such as a pier. They have also been effective in some cases in preventing the growth of barnacles, tube worms, and the like (so-called "hard fouling").

One biocide that has been investigated for use in marine paints and coatings to prevent or control soft fouling and hard fouling is DCOIT. However, the solubility of DCOIT is low in seawater and high in xylene. These properties have led paint manufacturers desiring to add DCOIT to marine paints to consider encapsulating DCOIT for incorporation into marine paints. DCOIT microcapsules are known in the art but the capsules reported in the literature to date have not been satisfactory. For example, xylene is a common solvent or base for marine paints. Unless the DCOIT capsules are essentially impermeable to xylene, the DCOIT may leak out of the capsules and react with the paint binders. This may cause viscosity increases in certain paint formulations or the DCOIT may cause undesirable plasticizing of the paint film. If the microcapsule is too permeable to water, the DCOIT may be leached away from the paint binder shortly after the paint film is applied rendering the paint vulnerable to attack by microorganisms at too early a stage in its service life. Accordingly, there is a need for improved encapsulated DCOIT compositions which provide in-can stability and yet gradually release the DCOIT in the marine environment.

SUMMARY OF INVENTION

Because DCOIT is an oily material with very low solubility in water that is liquid at temperatures at above about 40° C., certain embodiments of the invention utilize microencapsulation processes based upon oil-in-water emulsion systems.

In a further embodiment, the microcapsule shell or wall material is designed to be essentially impermeable to xylene. This affords good "in-can" stability, and reduces the tendency for the DCOIT to leach from the capsules and interact with or plasticize the paint binders in the dried marine film. The microcapsule shell should also be permeable to seawater. To achieve a good release rate of the microencapsulated DCOIT, the shell materials should be inherently hydrophilic such that they gradually release DCOIT to the surface of the marine coating in the presence of water and more particularly saltwater. In another embodiment of the invention, to enhance saltwater release, certain miscible organic solvents having partial water solubility are encapsulated with the DCOIT, to enhance the rate with which DCOIT is released from the film in water. In some embodiments, solvents such as dibasic esters, polyglycols and glycol ether acetates, and isobutyl isobutyrate can be used to form miscible DCOIT blends for encapsulation.

While the discussion herein addresses the encapsulation of DCOIT, those skilled in the art will recognize that other derivatives and analogues of DCOIT and combinations thereof with other biocides could be processed herein in a similar manner. In particular, other hydrophobic isothiazolones having low water solubility (e.g., less than 2% and more particularly less than 1% in water at room temperature) such as 2 n-octyl-3(2H)-isothiazolone (OIT) and benzisothiazolones (BIT) and their alkyl derivatives can be encapsulated alone or in combination with one another or other biocides using the teachings herein.

DETAILED DESCRIPTION OF INVENTION

DCOIT can be encapsulated in a number of wall materials to provide xylene in-can stability and to provide sustained release of the DCOIT upon exposure to water (i.e., natural water or saltwater). In a particular embodiment of the invention, the microcapsules are able to limit the release of the encapsulated DCOIT to less than 10% and preferably less than 5% in xylene at room temperature for 90 days. In other embodiments, the xylene impermeability is such that less than 10% and preferably less than 5% of DCOIT is released at 45° C. over 90 days.

In accordance with an embodiment of the invention a microcapsule having a wall formed from a hydrolyzed polyvinyl alcohol and phenolic resin is used for this purpose. In the case of microcapsules formed using partially hydrolyzed PVA, the hydrophilic character of the capsule shell can be adjusted by varying the amount of partially hydrolyzed PVA that is incorporated in the wall. In one embodiment, the partially hydrolyzed polyvinyl alcohol and the phenolic resin components (e.g., urea-rescorcinol-formaldehyde) are incorporated into the capsule shell in the amount of about 4 to about 8 parts by weight partially hydrolyzed PVA and about 20 to 30 parts phenolic resin. The encapsulation procedure for making these microcapsules is well known in the art and is illustrated in Example 1 . As illustrated in this example, to prevent the DCOIT from reacting with the wall materials, the DCOIT is mixed with a solvent diluent such as a substituted aromatic solvent like SAS 310 from Nisseki Chemical.

An amino-formaldehyde microcapsule (e.g. a melamine-formaldehyde (MF)) shell provides very stable microcapsules impermeable to xylene, but tends to be too impermeable in seawater to provide good bio-efficacy for use in conventional antifouling paints. It has been found that by optimizing the shell thickness, a balance of the desired properties of the microcapsules can be achieved. In one embodiment of the present invention, control of microcapsule shell thickness by particle size distribution and shell-to-core ratios contributes diffusion performance or sustained release characteristic. In one embodiment a microencapsulated DCOIT based on an amino-urea-formaldehyde shell system, the target wall thickness is about 0.1 to about 0.2 micron, or the shell to core ratio is about 0.03/1 to 0.05/1 by weight depending on the mean capsule diameter and overall capsule size distribution profile.

Partially hydrolyzed PVA functions as a dopant in the amino-urea formaldehyde wall. In accordance with one embodiment of the invention an agent referred to herein as a "dopant" is incorporated in the microcapsule wall to enhance the ability of water to leach the DCOIT from the capsule. According to one theory, the dopant interferes with the amino-urea-formaldehyde condensation reaction and cause hydrophilic defects in the microcapsule wall to facilitate the diffusion of the DCOIT. Representative examples of dopants include: partially and fully hydrolyzed PVAs, hydroxylethylcellulose, hydroxypropylcellulose, methylcellulose, hydroxyethylmethylcellulose, hydroxypropylmethylcellulose, hyroxybutylmethylcellulose, ethylhydroxyethylcellulose and polyethylene glycols. While the amount of dopant used will vary with the nature and thickness of the wall, in a particular embodiment the dopants are incorporated into the wall in an amount of about 2 to about 10% by weight based upon the weight of the wall materials. For capsules having thick walls, the amount of required dopant is expected to be more than the effective amount for thinner wall capsules.

In order to enhance natural water or saltwater release or extraction of the DCOIT, in one embodiment of the invention, the DCOIT is mixed with a partially water miscible solvent. Examples of partial water miscible solvents include esters and ethers and, more particularly, dibasic esters such as dimethyl adipate, or a blend of diisobutyl adipate, diisobutyl glutarate and diisobutyl succinate, polyglycol P-1200, and glycol ether EB acetate. Miscible organic solvents having partial water solubility in the range of approximately 0.5 to 5% in water are used in one embodiment of the invention. The upper range on the water solubility is not an absolute limit but reflects that if the solvent is more water soluble, it may move into the continuous phase and not remain with the DCOIT to enhance its water leachability. High boiling hydrophilic solvents, for example, having boiling points above 175° C. are desirable to use. If the boiling point of this solvent is too low, the solvent is difficult to retain in the microcapsule during the capsule drying operation. In a particular embodiment the higher boiling partially water miscible solvent is incorporated into the core in an amount of about 5 to about 50% and in other embodiments in an amount of about 10 to 25% by weight based upon the weight of the DCOIT.

In some embodiments a dual walled capsule has been used. In particular a dual encapsulation process with a first interfacial capsule wall of acrylic polymer and second wall of PVA-urea-resorcinol-gluteraldehyde can be used as illustrated in more detail in Example 3. The dual acrylic-PVA-URG system is advantageous because it provides a formaldehyde free product. Encapsulation based on PVA-URG or acrylic alone typically results in quite leaky capsules that are difficult to recover as a powder. However, combining the two systems to form hybrid capsule shells has resulted in dry free flow capsule powders.

Another embodiment of the present invention, uses a dual encapsulation process with a first interfacial capsule wall of acrylic polymer and PVA-urea-resorcinol-formaldehyde (URF) polymer is illustrated in Example 4. In still another embodiment of the present invention, dual wall microcapsules are formed comprising a first wall that is an interfacial reaction product of an aromatic polyisocyanate, a second wall of PVA-urea-resorcinol-formaldehyde(URF) condensation polymer is illustrated in Example 5. Other microcapsule wall systems that can be used in other embodiments of the present invention, include an MF shell capsule further re-encapsulated with PVA-URF (Example 6); an MF shell capsules re-encapsulated with PVA-urea-resorcinol-gluteraldehyde polymer (Example 7); a PVA-URF shell capsule re-encapsulated with an MF process; a hydrophilic shell comprising gelatin-gum arabic as a first shell and a overcoat of melamine-formaldehyde resin or a urea-resorcinol-formaldehyde condensation polymer (Examples 8 and 9).

Regarding the dual wall systems, the MF provides significant improvement in xylene stability while the PVA-URF or PVA-URG wall provides additional hydrophilicity in the shell to facilitate diffusion of the DCOIT in an aqueous environment. The dual wall system provides shell strength to minimize capsule damage during paint formulation and spray application to ship hulls. The ultimate shell characteristics for microencapsulated DCOIT are achieved by adjusting the thickness of the two wall materials to afford a balance of xylene stability and diffusion of DCOIT in seawater.

In another embodiment of the invention, the DCOIT is first encapsulated in a thin (e.g., less than about 0.1 micron) MF wall, and then further encapsulated in a PVA wall as described above. In this case the use of the solvent diluent like the SAS 310 may not be necessary for the encapsulation using the PVA-URF system since the MF wall prevents the DCOIT from reacting with the wall components. Thus, this dual encapsulation process allows the DCOIT to be encapsulated without the diluting effect of solvent and therefore affords a more cost effective product. Of course, the partially water miscible solvent may continue to be used with the DCOIT to enhance water leachability.

In one embodiment of the present invention, multi-shell microcapsules comprising an interfacial first wall with the reaction of an aromatic polyisocyanate, a second shell of gelatin-gum arabic and a third overcoat capsule wall of melamine-formaldehyde resin (Example 10). The 3-wall system of isocyanate/gelatin-gum arabic/MF is just another method of controlling capsule-wall permeability in an aqueous environment. The isocyanate-gelatin interface reduces premature diffusion of the DCOIT in the xylene-based paints. The interfacial reaction of polyisocyanate in conjunction with the PVA-URF provides another method of microencapsulating DCOIT. The interfacial skin of polyurethane or polyurea formed by the reaction of the isocyanate with the PVA or a polyamine provides an additional barrier for improving capsule stability in the xylene based MAF paints.

In accordance with one embodiment of the invention, the microcapsules should be small in order to be used in spray applications and to provide better distribution of the active ingredient in the paint film. In one embodiment, the capsule size range is about 5 microns to about 40 microns, and more typically about 5 microns to about 20 microns. Distribution of the biocide improves with smaller capsules such as less than 10 microns.

The microcapsules are usually dried before incorporating them into the paint formulation. Any conventional process for drying microcapsules including spray drying can be used for this purpose. However, for certain water-based paints, it will in some cases be possible to incorporate the microcapsules into the paint without drying.

In accordance with an embodiment of this invention, the encapsulated biocide is combined with a film former or binder such as the film formers and binders that have been proposed for use in marine paints, gel coats and the like (e.g., natural or synthetic resin or rosin binders) to provide coating compositions. In one embodiment of the invention, marine antifouling paint compositions can be prepared. Such paints can be prepared by incorporating the microcapsules described herein into the paint in an amount that is sufficient to impart the desired antifouling properties. Such amounts can be readily determined empirically by those skilled in the art. Examples of marine paints reported in the literature that are useful herein may contain about 5 to 50% by weight, or in other cases about 10 to 25% by weight, xylene or another solvent base, about 20 to 30% by weight zinc resinate to plasticize the resin binder, about 10 to 20% by weight resin binder, about 0 to 50%, or in other cases about 30 to 40% by weight, cuprous oxide pigment, and 4 to 6% by weight thixotropic viscosity modifier. Generally, the ingredients were thoroughly mixed as follows: 200 ml of the paint composition is introduced into a tight metallic container of 0.5 L capacity together with 100 ml (bulk volume) of glass beads with a diameter of 2-3 mm. The container is then shaken for 45 minutes on a mechanical shaker. The final paint composition is separated from the glass beads by filtration. The microencapsulated DCOIT biocide is incorporated in the paint in an amount to provide the marine antifouling properties that are desired (e.g., about 3 to 10% by weight). The amount required will be a function of the rate at which the DCOIT is leached from the microcapsules. In one embodiment, the capsules are added in an amount to provide about 2% DCOIT in the dry film.

Other applications for microencapsulated DCOIT may include use as a controlled release biocide in latex or oil-based paints and coatings, adhesives, sealants, caulks, mastic and patching materials, building materials, roofing materials such as shingles, plastics, polymer composites, paper processing, paper coatings, wood preservation, cooling water towers, metal working fluids, and as a general preservative. Additionally, while the discussion herein particularly addresses xylene based paints, the encapsulation techniques described herein may also be useful in providing solvent resistance and in-can stability for paints based on other solvents such as C-3 to C-10 ketones, more specifically C-5 to C-7 ketones (e.g., methyl isobutyl ketone (MIBK), isoamyl methyl ketone, hexanone, etc.); C-1 to C-10 alcohols, more specifically C-4 to C-6 alcohols (e.g., n-butanol and 2-butoxy ethanol); C-5 to C-50 aliphatic and aromatic hydrocarbons, more specifically C5-C32 hydrocarbons and still more specifically C5-C19 hydrocarbons (e.g., petroleum spirits, ethyl benzene, and trimethyl benzene); and for paints containing plasticizers such as phosphate esters and aromatic esters.

In accordance with another embodiment of the invention, a combination of two or more microcapsules can be used which release the biocide at different rates, for example, one microcapsule may be used that releases the biocide after or over a short time period and another microcapsule(s) might be used that releases the biocide after or over a somewhat longer time. These microcapsules may be made of different wall materials or different wall thicknesses in accordance with other embodiments of the invention.

The present invention is further illustrated by the following non-limiting examples.

EXAMPLE 1

Microencapsulation of Kathon 287T Biocide
Containing Solvent Diluent

An aqueous phase was prepared consisting of 160 grams each of a 5% strength aqueous solutions of polyvinyl alcohol, Vinol 540 and Vinol 125 (both manufactured by Air Products) and 300 grams of water. The aqueous phase is heated to 40° C.

The core material is prepared as a mixture of 100 grams of Kathon 287T (97%) manufactured by Rohm and Haas and 100 grams of a substituted aromatic solvent, SAS 310 manufactured by Nisseki Chemical and heated to 40° C. The aqueous phase and the core material are added to a 1-quart Waring Blender jar and the slurry is emulsified at moderate speed for about 15 minutes to produce an oil-in-water emulsion of droplets in the size range of about 10 to 40 microns. The emulsion is transferred to a 1-liter beaker. The slurry is slowly agitated using a turbine impellor while maintaining the temperature at about 40° C. A solution of 4 grams of urea and 10 grams of resorcinol in 60 grams of water is slowly added to the emulsion. A solution of 2 grams sodium sulfate in 30 grams of water is subsequently added to the slurry in drop-wise fashion. A 30 ml 37% formaldehyde solution is added drop-wise followed 10 minutes later by the addition of 20 ml of a 10% sulfuric acid solution over a 5-minute period. The slurry is warmed to 45° C. and after about one hour a solution of 4 g of urea, 6 g of resorcinol, 50 g of water and 20 ml of 37% formaldehyde second addition is added drop-wise. This solution may be divided, with half added in 15 minutes followed by a 15-minute hold period prior to adding the second half. One hour later another solution like the proceeding is added to the slurry in the same fashion. The slurry is heated to 55° C. and allowed to stir for 16 hours. The microcapsule slurry is cooled to ambient temperature and pH adjusted to 7.0 using 10% sodium hydroxide solution. The slurry is then diluted with water and strained using a 125-150 um sieve to remove encapsulated air and any debris. The slurry is set aside to allow the microcapsules to settle. The supernatant liquid is decanted and microcapsule concentrate is re-slurried with water. A small amount of Syloid 244 silica from W. R. Grace Company is stirred into the slurry; and the microcapsules are vacuum-filtered using Whatman 4.0 paper and tray dried to produce 230 grams of dry free-flowing powder. The resultant microcapsules are mostly 10-40 microns and can be incorporated in a marine coating composition to impart anti-fouling properties. The microcapsules were tested for stability in xlyene by placing a 50-mg sample into 50 mls of xlyene and periodically analyzing a small aliquot of the xylene spectrophotometrically for the presence of DCOIT to determine the amount diffused through the capsule shell. Samples were tested after room storage. 1.1% DCOIT was released after 56 days at room temperature.

EXAMPLE 2

Microencapsulation of Neat Kathon 287T Biocide

The microencapsulation of the neat Kathon 287T is carried out in an aqueous continuous phase to produce microcapules comprising an amino-formaldehyde shell. An aqueous phase is prepared consisting of 27.5 g of a 3.75% ethylene maleic anhyride co-polymer (manufactured by Zeeland Chemical Company) solution and 30.37 g of water and heated to 45° C. In a separate vessel, 32.5 g of Kathon 287T 97% manufactured by Rohm and Haas and is heated to 45° to form a liquid melt. An emulsion is prepared by dispersing the melted Kathon core material in the aqueous phase using an Ika-Works mixer and high speed turbine with the speed controlled to produce Kathon droplets mostly in the range of 10-50 um. While maintaining the temperature at 45° C. during the emulsification process, 5.58 grams of Cymel 385 manufactured by Cytec is added to stabilize the emulsion. After about 15 minutes, the agitation speed is reduced and additional 1.79 grams of the Cymel 385 resin is added while maintaining the temperature at around 50° C. After a few minutes, a 5-gram solution of a 5% polyvinyl alcohol Vinyl 540 manufactured by Air Products is added followed a drop-wise addition of 11 grams of a 15% salt solution of potassium dihydrogen phosphate over a 10 minute period. The temperature of the microcapsule slurry is slowly increased to 65° C. and 2.06 grams of urea is added about 1.5 hours after the salt addition. After an additional 4 hours of stirring at 65° C., the slurry is cooled to ambient and the ph adjusted to 7.0 using 45% potassium hydroxide solution. The slurry is diluted 1:1 with water and sieved using a 125 um sieve to remove encapsulated air and any debris. The microcapsules are allowed settle and the supernatant liquid decanted. The microcapsule concentrate is re-slurried in water and the decantation process repeated. The microcapsules are re-slurried with water; vacuum filtered using Whatman 4.0 paper; and tray dried either on the lab bench at ambient conditions or in a warm oven. The resultant microcapsules are a dry-free flowing powder that can be readily incorporated into a marine paint formulation to provide a marine coating in accordance with one embodiment of the invention. The microcapsules were tested using the xylene extraction test described in Example 1 and 1.4% DCOIT was released after 56 days at room temperature.

EXAMPLE 3A

Microencapsulation of DCOIT Biocide with a Dual Shell of Acrylic and PVA-urea-resorcinol-gluteraldehyde An internal phase is prepared by mixing together molten Kathon 287T (150 g) at a temperature of around 50° C., with methyl methacrylate (10 g) 1, 4, butanediol diacrylate (10 g) and trimethylolpropane trimethacrylate (10 g). Just prior to emulsification, tertbutyl perpivalate (1 g) is mixed in to the internal phase. The internal phase is homogenized into water (254 g) containing polyvinyl alcohol (Elvanol 50-42) (6 g) using a Waring 1 liter blender for 10 minutes until a stable emulsion is formed. The emulsion is then transferred into a 1-liter beaker with overhead stirring, thermometer and nitrogen supply and deoxygenated with nitrogen for 1 hour while heating to 90° C. The batch is then held at 90° C. for 1.5 hours after nitrogen removal before being cooled down to 45° C. The resulting emulsion contains polymeric particles each comprising a polymeric shell encapsulating the Kathon 287T having a mean particle size of 19 microns.

The particles of encapsulated Kathon 287T are then subjected to a secondary treatment at 45° C. involving drop wise additions of aluminum sulfate TG 8.3% (60 g) over 12 minutes, 10 v/v % sulfuric acid (34 g) over 12 minutes, and a mixture of urea (2 g), resorcinol (1.5 g), and water (20 g) over 12 minutes. Then a mixture of 25% gluteraldehyde (5 g) and water (5 g) are added drop wise very slowly over 20 minutes to prevent aggregation. Then a second addition of urea (2 g), resorcinol (1.5 g), and water (20 g) is added over 12 minutes followed by a mixture of 25% gluteraldehyde (5 g) and water (5 g) added drop wise over 12 minutes. Followed by a third addition of urea (2 g), resorcinol (1.5 g), and water (20 g) is added over 12 minutes followed by a mixture of 25% gluteraldehyde (5 g) and water (5 g) added drop wise over 12 minutes. After all additions are made the temperature is increased from 45° C. to 50° C. and held overnight to cure for approximately 16 hours. After cooling and pH neutralization the microcapsules are filtered and dried to produce a fine free flowing powder that can be readily incorporated into a marine paint formulation to provide a marine coating in accordance with one embodiment of the invention.

EXAMPLE 3B

Example 3A is repeated using a solution of sodium sulfate powder (2 g) dissolved in water (30 g) instead of aluminum sulfate. The sodium sulfate solution is added drop wise over 12 minutes. Again, a dry free flowing powder was achieved that can be readily incorporated into a marine paint formulation to provide a marine coating in accordance with one embodiment of the invention.

EXAMPLE 4

Dual Encapsulation Process with a First Interfacial Capsule Wall of Acrylic Polymer and PVA-urea-resorcinol-formaldehyde Polymer An internal phase is prepared by mixing together molten Kathon 287T (150 g) at a temperature of around 50° C., with methyl methacrylate (10 g) 1, 4, butanediol diacrylate (10 g) and trimethylolpropane trimethacrylate (10 g). Just prior to emulsification, tertbutyl perpivalate (1 g) is mixed in to the internal phase. The internal phase is homogenized into water (453 g) containing polyvinyl alcohol (Elvanol 50-42) (6 g) and (Elvanol 71-30) (6 g) using a Waring 1 liter blender for 8 minutes until a stable emulsion is formed. The emulsion is then transferred into a 1.5-liter beaker with overhead stirring, thermometer and nitrogen supply and deoxygenated with nitrogen for 1 hour while heating to 90° C. The batch is then held at 90° C. for 1.5 hours after nitrogen removal before being cooled down to 40° C. The resulting emulsion contains polymeric particles each comprising a polymeric shell encapsulating the Kathon 287T having a mean particle size of 19 microns. The particles of encapsulated Kathon 287T are then subjected to a secondary treatment at 40° C. involving drop wise addition of a mixture of urea (3 g), resorcinol (7.5 g), and water (45 g) over 12 minutes. Then a solution of sodium sulfate powder (1.5 g) and water (22.5 g) is added drop wise over 10 minutes. Then a 37% solution of formaldehyde (22.5 ml) is added drop wise over 10 minutes. After a 10-minute hold at 40° C., 10 v/v % sulfuric acid is added drop wise over 6 minutes. The batch is then stirred and slowly heated to 45° C. over 1 hour. Then a second addition of a solution of urea (3 g), resorcinol (4.5 g), water (37.5 g) and 37% formaldehyde (15 ml) is divided in half and added over 12 minutes followed by the second half after a 15 minute hold at 45° C. The batch is then stirred and slowly heated to 48° C. over 1 hour. A third addition of urea (3 g), resorcinol (4.5 g), water (37.5 g) and 37% formaldehyde (15 ml) is added over 12 minutes. After all additions are made the temperature is increased from 48° C. to 50° C. and held overnight to cure for approximately 16 hours. After cooling and pH neutralization the microcapsules are filtered and dried to produce a dry product that can be readily incorporated into a marine paint formulation to provide a marine coating in accordance with one embodiment of the invention.

EXAMPLE 5

Dual Wall Microcapsules Comprising an Interfacial First Wall with the Reaction of an Aromatic Polyisocyanate, a Second Shell of PVA-urea-resorcinol-formaldehyde Condensation Polymer An internal phase is prepared by mixing together molten Kathon 287T (90 g) at a temperature of around 50° C., with Desmodur L 75 (Bayer) (10 g). The internal phase is homogenized into water (302 g) containing polyvinyl alcohol (Elvanol 50-42) (4 g) and (Elvanol 71-30) (4 g) using a Waring 1 liter blender for 13 minutes until a stable emulsion is formed. The emulsion is then transferred into a 1-liter beaker with overhead stirring and thermometer. The batch is then heated to 50° C. and a solution of triethylene diamine (0.5 g) and water (10 g) is added drop wise. The batch is then held at 50° C. overnight. The resulting emulsion contains polymeric particles each comprising a polymeric poly urea shell encapsulating the Kathon 287T having a mean particle size of 16 microns. The particles of encapsulated Kathon 287T are then subjected to a secondary treatment at 40° C. involving drop wise addition of a mixture of urea (2 g), resorcinol (5 g), and water (30 g) over 12 minutes. Then a solution of sodium sulfate powder (1 g) and water (15 g) is added drop wise over 6 minutes. Then a 37% solution of formaldehyde (15 ml) is added drop wise over 7 minutes. After a 10-minute hold at 40° C., 10 v/v % sulfuric acid is added drop wise over 5 minutes. The batch is then stirred and slowly heated to 45° C. over 1 hour. Then a second addition of a solution of urea (2 g), resorcinol (3 g), water (25 g) and 37% formaldehyde (10 ml) is divided in half and added over 12 minutes followed by the second half after a 15 minute hold at 45° C. The batch is then stirred and slowly heated to 48° C. over 1 hour. A third addition of urea (2 g), resorcinol (3 g), water (25 g) and 37% formaldehyde (10 ml) is added over 12 minutes. After all additions are made the temperature is increased from 48° C. to 50° C. and held overnight to cure for approximately 16 hours. After cooling and pH neutralization the microcapsules are filtered and dried to produce a lumpy isolation.

EXAMPLE 6

MF Shell Capsules Re-Encapsulated with PVA-URF Polymer

An internal phase is prepared by melting Kathon 287T (260 g) at a temperature of around 50° C. The internal phase is homogenized into an aqueous A Solution consisting of 110.0 g of a 3.75% ethylene maleic anhydride copolymer solution and 121.48 g of water using a Waring 1 liter blender. While maintaining the temperature of around 50° C. during the emulsification process, Cymel 385 (22.33 g) manufactured by Cytec is added to stabilize the emulsion. After about 15 minutes, the agitation is reduced and 10-50 um droplets are formed. The emulsion is then transferred into a 1-liter beaker with overhead stirring and thermometer. Then a 15% salt solution (44 g) of potassium dihydrogen phosphate is added drop wise. The batch is then heated to 65° C. over 1.5 hours and held for 4 hour then cooled. The resulting emulsion contains polymeric particles each comprising a polymeric amino-formaldehyde shell encapsulating the Kathon 287T having a mean particle size of 16 microns.

The particles of encapsulated Kathon 287T slurry are then divided in half. This (272 g) fraction is subjected to a secondary treatment at 45° C. involving drop wise addition of a mixture of urea (3 g), resorcinol (3 g), and water (30 g) over 10 minutes. Then a 37% solution of formaldehyde (18 ml) is added drop wise over 7 minutes. After a 10-minute hold at 45° C., 10 v/v % sulfuric acid (10 ml) is added drop wise over 5 minutes. The batch is then stirred at 45° C. over 1 hour. Then a second addition of a solution of urea (3 g), resorcinol (7 g), water (30 g) and 37% formaldehyde (25 ml) is divided in half and added over 12 minutes followed by the second half after a 15 minute hold at 45° C. The batch is then stirred and slowly heated to 55° C. over 1 hour. Then heated to 60° C. for 3 hours and cooled. After cooling and pH neutralization the microcapsules are filtered and dried to produce a fine free flowing powder that can be readily incorporated into a marine paint formulation to provide a marine coating in accordance with one embodiment of the invention. The microcapsules were tested using the xylene extraction test described in Example 1 except that a sample of the microcapsules was also tested at 45° C. In this test 0.4% DCOIT was released after 28 days at room temperature and 2.7% DCOIT was released after 28 days at 45° C.

EXAMPLE 7A

MF Shell Capsules Re-Encapsulated with PVA-urea-resorcinol-gluteraldehyde Polymer An internal phase is prepared by melting Kathon 287T (260 g) at a temperature of around 50° C. The internal phase is homogenized into an aqueous solution consisting of 110.0 g of a 3.75% ethylene maleic anhydride copolymer solution and 121.48 g of water using a Waring 1 liter blender. While maintaining the temperature of around 50° C. during the emulsification process, Cymel 385 (22.33 g) manufactured by Cytec is added to stabilize the emulsion. After about 15 minutes, the agitation is reduced and 10-50 um droplets are formed. The emulsion is then transferred into a 1-liter beaker with overhead stirring and thermometer. Then a 15% salt solution (44 g) of potassium dihydrogen phosphate is added drop wise. The batch is then heated to 65° C. over 1.5 hours and held for 4 hour then cooled. The resulting emulsion contains polymeric particles each comprising a polymeric amino-formaldehyde shell encapsulating the Kathon 287T having a mean particle size of 16 microns. The particles of encapsulated Kathon 287T slurry are then divided and half are filtered to a wet cake of 80.51% (127.5 g dry wt.). The wet cake is then re-suspended in a mixture of water (254 g) containing polyvinyl alcohol (Elvanol 50-42) (6 g) and subjected to a secondary treatment at 45° C. involving drop wise additions of aluminum sulfate TG 8.3% (60g) over 12 minutes, 10 v/v % sulfuric acid (34 g) over 12 minutes, and a mixture of urea (2 g), resorcinol (1.5 g), and water (20 g) over 12 minutes. Then a mixture of 25% gluteraldehyde (5 g) and water (5 g) are added drop wise very slowly over 20 minutes to prevent aggregation. Then a second addition of urea (2 g), resorcinol (1.5 g), and water (20 g) is added over 12 minutes followed by a mixture of 25% gluteraldehyde (5 g) and water (5 g) added drop wise over 12 minutes. Followed by a third addition of urea (2 g), resorcinol (1.5 g), and water (20 g) is added over 12 minutes followed by a mixture of 25% gluteraldehyde (5 g) and water (5 g) added drop wise over 12 minutes. After all additions are made the temperature is increased from 45° C. to 50° C. and held overnight to cure for approximately 16 hours. After cooling and pH neutralization the microcapsules are filtered and dried to produce a fine free flowing powder that can be readily incorporated into a marine paint formulation to provide a marine coating in accordance with one embodiment of the invention. The microcapsules were tested using the xylene extraction test described in Example 1 except that a sample of the microcapsules was also tested at 45° C. In this test 2.4% DCOIT was released after 14 days at room temperature and 3% DCOIT was released after 14 days at 45° C.

EXAMPLE 7B

Example 7A is repeated using a solution of sodium sulfate powder (2 g) dissolved in water (30 g) instead of aluminum sulfate. The sodium sulfate solution is added drop wise over 12 minutes. Again, a dry free flowing powder was produced that can be readily incorporated into a marine paint formulation to provide a marine coating in accordance with one embodiment of the invention.

EXAMPLE 8

Dual Encapsulation with Gelatin/Gum Arabic as the First Shell and Melamine Resin as the Second Wall In a 1000 ml beaker fitted with an Ika-Works mixer and 4-blade turbine impellor, dissolve 6 grams 300 bloom gelatin and 6 grams spray dried gum arabic in 240 ml deionized water. Start mixing at room temperature, again and heat to 80° C. with stirring.

Adjust the pH to clear the solution with 10% NaOH (~pH 7). Adjust the pH to 4.1 with 10% Acetic Acid. Warm 40 grams Kathon 287T to 50-60° C. to melt. Transfer the Gelatin/Gum Arabic solution to a warm blender jar and add the Kathon 287T melt. Emulsify slowly (~10 min) to achieve the desired droplet size (10-40 microns). Transfer back to the beaker-mixer apparatus in an empty water bath. Using a separatory funnel, about 175 ml warm (50-60° C.) deionized water was added drop-wise. Check with a microscope to observe liquid-liquid phase separation of a fluid phase that partially wraps the droplets. Adjust the amount of deionized water up or down to achieve this result. Begin slow cooling the beaker by adding a few ice cubes to the water bath. At 35° C., the fluid polymer phase should be observed microscopically. Continue slow cooling to 28° C. Check microscopically again to verify if the solution is mostly clear with a noticeable wall formation and little free polymer. Continue slow cooling to 25° C. One should observe a substantial wall and no free polymer. Continue cooling to 15° C., at which time 10 grams of 25% gluteraldehyde is added. After adding more ice, stir overnight, allowing the reaction to warm to room temperature. Decant 2 times by letting capsules settle and rinsing with 300 ml deionized water. Capsules can be isolated at this point by filtering and adding 1.5 grams Aerosil 972R to the filter-cake and shaking in a wide-mouth bottle to mix well. The powder is laid out on a paper towel to bench-dry overnight. This resulted in a free flowing powder with single (droplet) capsules as well as some aggregates.

A second wall can be added by filtering the twice-decanted slurry. The wet filter-cake is re-suspended in 25 grams of 3.75% EMA solution and 50 ml deionized water. Begin heating to 50° C. and while dripping in 3 grams Cymel 385 in 12 ml deionized water. At 50° C., drop-wise, add 10 grams 15% dihydrogen phosphate solution. Heat to 65° C. and hold over night. Cool to room temperature and adjust the pH to 7.0 with 45% Potassium Hydroxide solution. Filter, and wash with deionized water. Spread out on a paper towel to dry. This resulted in a free flowing powder with single (droplet) capsules as well as some aggregates.

EXAMPLE 9

Dual Encapsulation with Gelatin/Gum Arabic as the First Shell and Urea-resorcinol-formaldehyde Polycondensate as the Second Wall In a 1000 ml beaker fitted with an Ika-Works mixer and 4-blade turbine impellor, dissolve 6 grams 300 bloom gelatin and 6 grams spray dried gum arabic in 240 ml deionized water. Start mixing at room temperature, again and heat to 80° C. with stirring.

Adjust the pH to clear the solution with 10% NaOH (~pH 7). Adjust the pH to 4.1 with 10% Acetic Acid. Warm 40 grams Kathon 287T to 50-60° C. to melt. Transfer the Gelatin/Gum Arabic solution to a warm blender jar and add the Kathon 287T melt. Emulsify slowly (~10 min) to achieve the desired droplet size (10-40 microns). Transfer back to the beaker-mixer apparatus in an empty water bath. Using a separatory funnel, about 175 ml warm (50-60° C.) deionized water was added drop-wise. Check with a microscope to observe liquid-liquid phase separation of a fluid phase that partially wraps the droplets. Adjust the amount of deionized water up or down to achieve this result. Begin slow cooling the beaker by adding a few ice cubes to the water bath. At 35° C., the fluid polymer phase should be observed microscopically. Continue slow cooling to 28° C. Check microscopically again to verify if the solution is mostly clear with a noticeable wall formation and little free polymer. Continue slow cooling to 25°. One should observe a substantial wall and no free polymer. Continue cooling to 15° C., at which time 10 grams of 25% gluteraldehyde is added. After adding more ice, stir overnight, allowing the reaction to warm to room temperature. Decant 2 times by letting capsules settle and rinsing with 300 ml deionized water. Capsules can be isolated at this point by filtering and adding 1.5 grams Aerosil 972R to the filter-cake and shaking in a wide-mouth bottle to mix well. The powder is laid out on a paper towel to bench-dry overnight. This resulted in a free flowing powder with single (droplet) capsules as well as some aggregates. A second wall can be added by filtering the twice-decanted slurry. The wet filter-cake is re-suspended in 25 grams of 3.75% EMA solution and 50 ml deionized water. Begin heating to 50° C. and while dripping in 2 grams Urea and 0.2 grams resorcinol in 10 ml deionized water. At 50° C., drop-wise, add 5 grams 37% Formaldehyde solution then 10 grams 15% dihydrogen phosphate solution. Heat to 55° C. and hold over night. Cool to room temperature and adjust the pH to 7.0 with 45% Potassium Hydroxide solution. Filter, and wash with deionized water. Spread out on a paper towel to dry. This resulted in a free flowing powder with single (droplet) capsules as well as some aggregates.

EXAMPLE 10

Multi-shell Microcapsules Comprising polyurethane/polyurea, Gelatin/Gum Arabic and Melamine Resin In a 1000 ml beaker fitted with an Ika-Works mixer and 4-blade turbine impellor, dissolve 6 grams 300 bloom gelatin and 6 grams spray dried gum arabic in 240 ml deionized water. Start mixing at room temperature, again and heat to 80° C. with stirring.

Adjust the pH to clear the solution with 10% NaOH (~pH 7). Adjust the pH to 4.1 with 10% Acetic Acid. Warm 40 grams Kathon 287T to 50-60° C. to melt. Add 4 grams Desmondure CB-75 and mix well. Transfer the Gelatin/Gum Arabic solution to a warm blender jar and add the Kathon 287T solution. Emulsify slowly (~10 min) to achieve the desired droplet size (10-40 microns). Transfer back to the beaker-mixer apparatus in an empty water bath. Using a separatory funnel, about 175 ml warm (50-60° C.) deionized water was added drop-wise. Check with a microscope to observe liquid-liquid phase separation of a fluid phase that partially wraps the droplets. Adjust the amount of deionized water up or down to achieve this result. Begin slow cooling the beaker by adding a few ice cubes to the water bath. At 35° C., the fluid polymer phase should be observed microscopically. Continue slow cooling to 28° C. Check microscopically again to verify if the solution is mostly clear with a noticeable wall formation and little free polymer. Continue slow cooling to 25° C. One should observe a substantial wall and no free polymer. Continue cooling to 15° C., at which time 10 grams of 25% gluteraldehyde is added. After adding more ice, stir overnight, allowing the reaction to warm to room temperature.

Decant 2 times by letting capsules settle and rinsing with 300 ml deionized water. Capsules can be isolated at this point by filtering and adding 1.5 grams Aerosil 972R to the filter-cake and shaking in a wide-mouth bottle to mix well. The powder is laid out on a paper towel to bench-dry overnight. This resulted in a free flowing powder with single (droplet) capsules as well as some aggregates. A third wall can be added by filtering the twice-decanted slurry. The wet filter-cake is re-suspended in 25 grams of 3.75% EMA solution and 50 ml deionized water. Begin heating to 50° C. and while dripping in 3 grams Cymel 385 in 12 ml deionized water. At 50° C., drop-wise, add 10 grams 15% dihydrogen phosphate solution. Heat to 65° C. and hold over night. Cool to room temperature and adjust the pH to 7.0 with 45% Potassium Hydroxide solution. Filter, and wash with deionized water. Spread out on a paper towel to dry. This resulted in a free flowing powder with single (droplet) capsules as well as some aggregates.

Having described the invention in detail and with reference to specific advantages thereof it will be apparent that numerous modifications are possible without departing from the spirit and scope of the following claims.

What is claimed is:

1. A microencapsulated biocide comprising an isothiazolone biocide or antifouling agent as a core material encapsulated in a wall material that has a xylene impermeability such that less than 10% of the biocide or antifouling agent is released from the capsule at room temperature to 45° C. over 90 days and from which water or saltwater can leach the biocide from the wall material, wherein the wall material contains a dopant to enhance the diffusion of isothiazolone from the capsule and is a reaction product of polyvinyl alcohol, urea, resorcinol, and formaldehyde resin.

2. The microencapsulated biocide of claim 1 wherein the isothiazolone includes 4,5-dichloro-2-n-octyl-3(2H)-isothiazolone.

3. The microencapsulated biocide of claim 2 wherein the isothiazolone is present in the core dissolved in a partially water soluble solvent.

4. The microencapsulated biocide of claim 1 wherein the dopant is polyvinyl alcohol.

5. The microencapsulated biocide of claim 3 wherein the partially water soluble solvent dissolves in water in an amount of about 0.5 to about 5% and is incorporated into the core in an amount of about 5 to about 25%.

6. The microencapsulated biocide of claim 5 wherein the solvent is an ester or an ether or mixtures thereof.

7. The microencapsulated biocide of claim 1 wherein the wall material is a dual wall microcapsule including a melamine-formaldehyde inner wall.

8. The microencapsulated biocide of claim 1 wherein the dopant is selected from the group consisting of polyvinyl alcohol, hydroxylethylcellulose, hydroxypropylcellulose, methylcellulose, hydroxyethylmethylcellulose, hydroxypropylmethylcellulose, hyroxybutylmethylcellulose, ethylhydroxyethylcellulose, and polyethylene glycols.

9. The microencapsulated biocide of claim 1 wherein the wall material is a dual wall having an inner wall and an outer wall.

10. The microencapsulated biocide 9 wherein the inner wall includes is an acrylic polymer and the outer wall is a PVA-urea-resorcinol-formaldehyde(URF) polymer.

11. The microencapsulated biocide of claim 9 wherein the inner wall is an interfacial reaction product of an aromatic polyisocyanate and the outer wall is a PVA-urea-resorcinol-formaldehye(URF) condensation polymer.

12. The microencapsulated biocide of claim 9 wherein the inner wall is a melamine-formaldehyde and the outer wall is a PVA-urea-resorcinol-formaldehye(URF) polymer.

* * * * *

UNITED STATES PATENT AND TRADEMARK OFFICE
CERTIFICATE OF CORRECTION

PATENT NO. : 7,550,200 B2  
APPLICATION NO. : 11/226644  
DATED : June 23, 2009  
INVENTOR(S) : Hart et al.

Page 1 of 1

It is certified that error appears in the above-identified patent and that said Letters Patent is hereby corrected as shown below:

Claim 10, Col. 14, Line 25, after "biocide" insert -- of claim --.

Claim 10, Col. 14, Line 26, delete "includes".

Claim 11, Col. 14, Line 31, "formaldehye(URF)" should read -- formaldehyde(URF) --.

Claim 12, Col. 14, Line 34, "formaldehye(URF)" should read -- formaldehyde(URF) --.

Signed and Sealed this

Eighth Day of September, 2009

David J. Kappos
*Director of the United States Patent and Trademark Office*